(12) United States Patent
Kwak et al.

(10) Patent No.: US 7,314,644 B2
(45) Date of Patent: Jan. 1, 2008

(54) **EXTRACTION AND PURIFICATION METHOD OF ACTIVE CONSTITUENTS FROM STEM OF *LONICERA JAPONICA* THUNB., ITS USAGE FOR ANTI-INFLAMMATORY AND ANALGESIC DRUG**

(75) Inventors: Wie-Jong Kwak, Seoul (KR); Yong-Baik Cho, Anyang-shi (KR); Chang-Kyun Han, Seoul (KR); Hee Jae Shin, Suwon-shi (KR); Keun Ho Ryu, Seoul (KR); Hunseung Yoo, Seoul (KR); Hae In Rhee, Seoul (KR)

(73) Assignee: SK Chemicals Co., Ltd., Kyungki-do (KR)

( * ) Notice: Subject to any disclaimer, the term of this patent is extended or adjusted under 35 U.S.C. 154(b) by 206 days.

(21) Appl. No.: 10/527,139

(22) PCT Filed: Sep. 8, 2003

(86) PCT No.: PCT/KR03/01851

§ 371 (c)(1),
(2), (4) Date: Mar. 8, 2005

(87) PCT Pub. No.: WO2004/024172

PCT Pub. Date: Mar. 25, 2004

(65) Prior Publication Data

US 2006/0014240 A1    Jan. 19, 2006

(30) Foreign Application Priority Data

Sep. 11, 2002  (KR) ................... 10-2002-0055106
Sep. 26, 2002  (KR) ................... 10-2002-0058494

(51) Int. Cl.
*A01K 65/00* (2006.01)
(52) U.S. Cl. .................................. 424/779
(58) Field of Classification Search ............. None
See application file for complete search history.

(56) References Cited

FOREIGN PATENT DOCUMENTS

CN         1616403 A    *  5/2005
KR    1998-0163813 B1    12/1998
KR    2001-0267060 B1     3/2001

OTHER PUBLICATIONS

Prasad et al., A new secoiridoid glycoside from *Lonicera augustifolia*, Fitoterapia vol. 71, 2002, pp. 420-424.*
Machida et al., Studies on the Constituents of Lonicera Species. XVII. New Iridoid Glycosides of the Stems and Leaves of *Lonicera japonica* Thunb, Chem.Pharm. Bull. vol. 50(8), 2002, pp. 1041-1044.*
Lee, Song Jin et al., "Anti-inflammatory Activity of the Major Constituents of *Lonicera japonica*" Arch. Pharm. Res. 1995;18(2): pp. 133-135.
Lee, S.J. et al., "Antiinflammatory Activity of *Lonicera japonica*" Phytotherapy Research. vol. 12, 1998, pp. 445-447.
Recio, MC et al., "Structural considerations on the iridoids as anti-inflammatory agents", Planta Med. Jun. 1994; 60(3): Abstract Only of pp. 232-234.
Kwak, Wie Jong et al., "Loniceroside C, an Antiinflammatory Saponin from *Lonicera japonica*" Chem. Pharm.Bull. vol. 51(No. 3) Mar. 2003; pp. 333-335.
Moon, Tae Chul et al., "Anti-inflammatory Activity of the Flavonoid Components of *Lonicera japonica*" J. Pharm. Soc. Korea 1999, vol. 43 (No. 1): pp. 117-123.
Tae, J. et al., "Anti-inflammatory effect of *Lonicera japonica* in proteinase-activated receptor 2-mediated paw edema." Clin. Chim. Acta Apr. 2003 (1-2): Abstract only of pp. 165-171.

* cited by examiner

*Primary Examiner*—Christopher R. Tate
*Assistant Examiner*—Deborah A. Davis
(74) *Attorney, Agent, or Firm*—Frommer Lawrence & Haug LLP; Ronald R. Santucci (57) ABSTRACT

Disclosed is a method for extracting and purifying active constituents from honeysuckle (*Lonicera japonica* Thunb.) and its use. More particularly, this invention relates to an extraction and purification method of active constituents including sweroside from for honeysuckle stem (stem of honeysuckle where leaves are removed) by removing tannins, hardly soluble flavonoids, saponins, and the like. Thus obtained active constituents have better anti-inflammatory and analgesic effect, are safer and more stable than the conventional active constituents obtained from honeysuckle flower or honeysuckle leaves, and include sweroside which is an effective active ingredient of anti-inflammatory and analgesic drug.

7 Claims, 2 Drawing Sheets

**EXTRACTION AND PURIFICATION METHOD OF ACTIVE CONSTITUENTS FROM STEM OF *LONICERA JAPONICA* THUNB., ITS USAGE FOR ANTI-INFLAMMATORY AND ANALGESIC DRUG**

This application is a 371 of PCT/KR2003/001851 filed on Sep. 8, 2003, published on Mar. 25, 2004 under publication number WO 2004/024172 A1 which claims priority benefits from South Korean Patent Application Number 10-2002-0055106 filed Sep. 11, 2002 and South Korean Patent Application Number 10-2002-005 8494 filed Sep. 26, 2002.

BACKGROUND OF THE INVENTION

1. Field of the Invention

The present invention relates to an extraction and purification method of active constituents from honeysuckle (*Lonicera japonica* Thunb.) and its use, more particularly to an extraction and purification method of active constituents including sweroside from honeysuckle stem (stem of honeysuckle where leaves are removed) by removing tannins, hardly soluble flavonoids, saponins, and the like. Thus obtained active constituents have better anti-inflammatory and analgesic effect, are safer and more stable than the conventional active constituents obtained from honeysuckle flower or honeysuckle leaves, and include sweroside which is an effective active ingredient of anti-inflammatory and analgesic drug.

The honeysuckle (*Lonicera japonica* Thunb.) is a semi-evergreen viny shrub that grows naturally at the feet of mountains or levees in the range of an altitude of 50 to 600 meters in Japan, China and Korea. Its flower bud (honeysuckle flower) and stem (honeysuckle stem) are used as herbal medicines for promotion of urination, detoxification, hemostasis, blood purification, treatment of tumor, edema treatment, cold, diarrhea, emesis, and the like [Illustrated Book of Korean Flora, Chang-Bok Lee, 709, 1989, Hangmun Publishing Co., Seoul; Standard for Herbs (Herb Medicines) Not Covered by Korean Pharmacopoeia, Hyung-Joon Chi, Sang-In Lee, 87, 305, 1988, Korea Medical Index Co., Seoul; Resource Plants in Korea, Tae-Kyung Kim, vol. 4, 148-149, 1996, SNU Press, Seoul]. Also, many traditional Chinese medicinal books including Sasang Constitutional Medicine and Gwangje Bigeup teach that it is good for treating a variety of inflammatory abscesses inside and outside human bodies [Sasang Constitutional Medicine for Chosun People, Yenben Chosun Medical Institute, 276, 1991, Yeogang Publishing Co., Seoul; Gwangje Bigeup, Kyung-Hwa Lee, 349-351, 1991, Yeogang Publishing Co., Seoul]. It has long been used as a folk remedy for treatment of upper respiratory infections such as cold, tonsillitis and neuralgia for its anti-inflammatory and analgesic activity. Recently, the inflammatory and analgesic activity of honeysuckle has been proved through a variety of experimental animal models, and its effective physiologically active constituents have been isolated and reported to the academic circle [Development of the vegetable anti-inflammatory medicine: Comparison of anti-inflammatory and analgesic actions of the honeysuckle extract, Song-Jin Lee et al., *Korean Journal of Pharmacognosy*, 363-367, 25, 1994; Flavonoids from the aerial parts of *Lonicera japonica*, Son et al., *Arch. Pharm. Res.*, 365-370, 15, 1992; Antiinflammatory activity of *Lonicera japonica*, Lee et al., *Phytother. Res.*, 445-447, 12, 1998; Triterpenoid saponins from the aerial parts of *Lonicera japonica*, Son et al., *Phytochem.*, 1005-1008, 35, 1994 ; Anti-inflammatory activity of the major constituents of *Lonicera japonica*, Lee et al., *Arch. Pharm. Res.*, 133-135, 18, 1995].

2. Description of the Related Art

To date, hydrolyzable tannins such as caffeoylquinic acid, methyl caffeate, chlorogenic acid and iso-chlorogenic acid, and iridoid glycosides such as loganin, sweroside, vogeloside and epi-vogeloside are known as effective active constituents contained in honeysuckle stem. Most conventional researches have been centered on honeysuckle flower and honeysuckle leaves. It should be noted that honeysuckle stem has a different distribution of constituents from honeysuckle leaves or honeysuckle flower. That is, unlike honeysuckle stem, major constituents of honeysuckle leaves or honeysuckle flower are flavonoids, such as lonicerin, rhoifolin and ochnaflavon, triterpene saponins having hederagenin or oleanolic acid as non-sugar constituent, and various hydrolyzable tannins.

These constituents are hard to be prepared into an injection. If the injection is rich in polymer tannins, they may bind to other constituents thus resulting in coprecipitation, and may bind to serum proteins in the blood to form hardly soluble precipitates, which can be a cause of angiostenosis. In addition, since flavonoids included in honeysuckle in general are insoluble to water, a fairly large amount of organic solvent or other agents which mediate dissolution are necessary to dissolve them to the level higher than the effective concentration. Also, active constituents rich in flavonoids are extremely insoluble in physiological salt solution for injection and may become unstable if stored for a long time in an alkaline buffer solution. Lastly, saponins obtained from honeysuckle, particularly monodesmosides, are known to have strong hemolysis properties. Therefore, they cannot be injected directly into the vein without purification [Studies on the saponins of *Lonicera japonica* Thunb., Kawai et al., *Chem. Pharm. Bull.*, 4769-4775, 36(12), 1988]. Honeysuckle leaves and honeysuckle flower are greater in tannins and hardly soluble flavonoids than honeysuckle stem. In the acute toxicity test for injections, they confer more toxicity than honeysuckle stem even at low contents, and provide poor analgesic and anti-inflammatory effect.

*Lonicera japonica*, *Swertia japonica*, *Gentiana scabra*, *Gentiana triflora*, *Gentiana manshurica*, *Gentiana rigescens*, and *Gentiana rigescens* French. var. stictantha Marquand have been used for alleviation of fever or detoxification for many years. However, it has not been clearly understood which constituents offer such effects, and most of the researches have been concentrated on identifying the activities of loganin, the major medicinal ingredient of honeysuckle stem [*J. Nat. Prod.*, 54(4), 1102~1104, 1991: *Planta Med.*, 60, 232~234, 1994: *Phytotherapy Res.*, 12, 405-408, 1998].

Further, sweroside has been known as effective only in liver protection and inhibition of bacterial activity [*J. Ethnopharmacol.*, 42, 183-191, 1994: *Chem. Pharm. Bull.*, 45(11), 1823-1827, 1997: *Yakugaku Zasshi*, 102(8), 755-759, 1982], and its anti-inflammatory and analgesic effect has not been reported so far.

SUMMARY OF THE INVENTION

The present inventors have identified that active constituents of honeysuckle stem (stem of honeysuckle where leaves are removed), from which tannins, hardly soluble flavonoids, saponins, and the like have been removed, and sweroside, the effective active ingredient of the active constituents, have superior anti-inflammatory and analgesic effect.

Accordingly, it is an object of the present invention to provide a preparation method for preparing active constituents from honeysuckle stem, which have superior anti-inflammatory and analgesic activity, safety and stability.

It is another object of the present invention to provide an anti-inflammatory and analgesic drug comprising the active constituents.

It is still another object of the present invention to provide an anti-inflammatory and analgesic drug comprising sweroside.

BRIEF DESCRIPTION OF THE DRAWING

FIG. 1 is a graph that shows medicinal effects of the active constituents depending on their contents.

DETAILED DESCRIPTION OF THE PREFERRED EMBODIMENTS

Figure 1A:
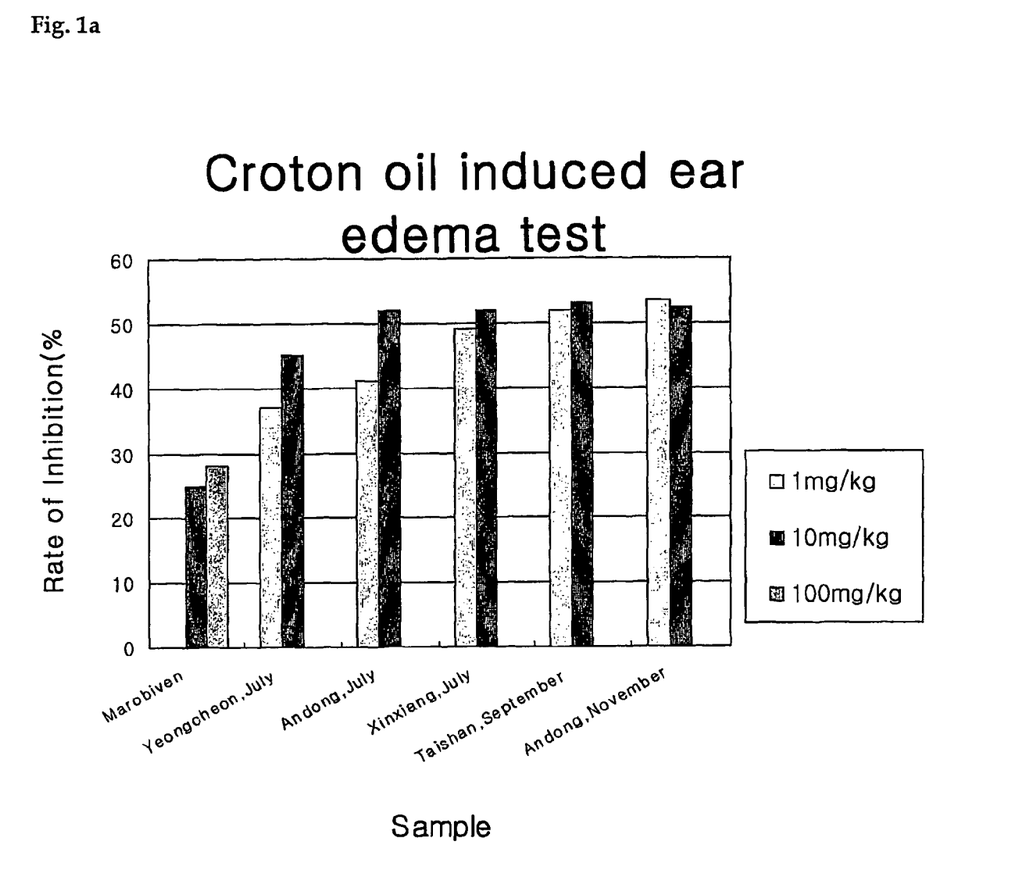
Figure 1B:
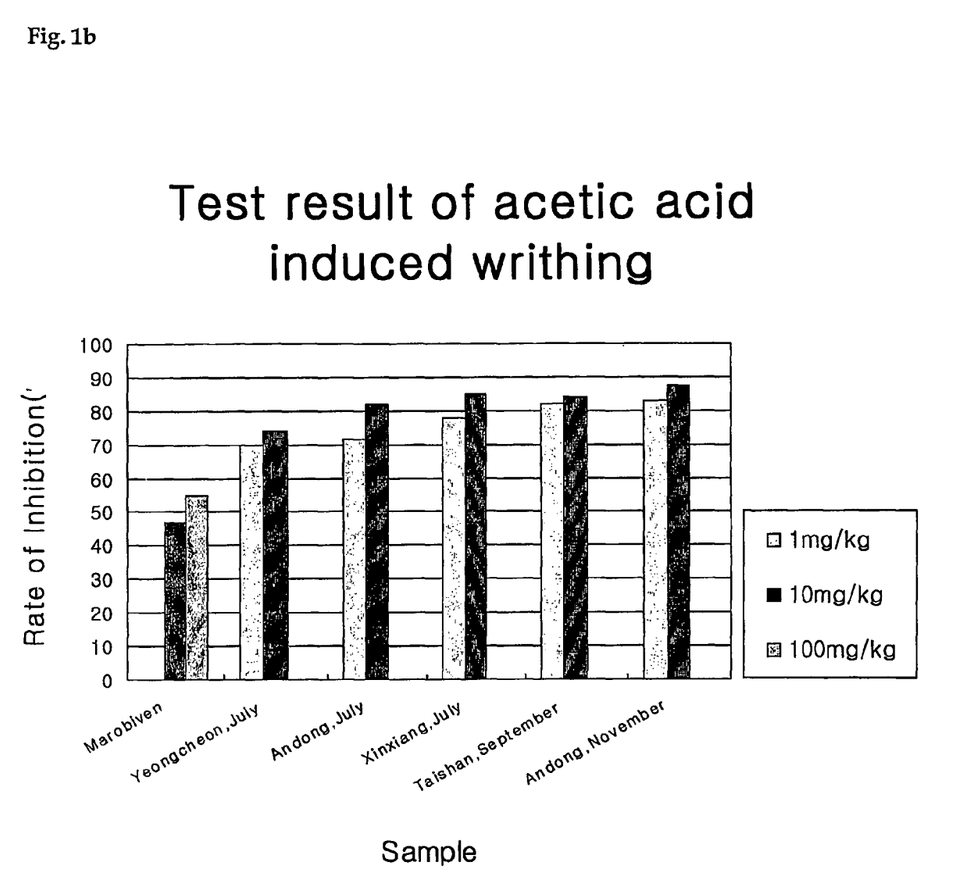

The present invention provides a method for preparing active constituents from honeysuckle stem, which have superior anti-inflammatory and analgesic activity, safety and stability.

The present invention also provides an anti-inflammatory and analgesic drug comprising the active constituents.

The present invention also provides an anti-inflammatory and analgesic drug comprising sweroside.

Hereunder is given a more detailed description of the present invention.

The present invention relates to a method extracting and purifying active constituents and sweroside from honeysuckle by removing tannins, hardly soluble flavonoids, saponins, and the like. Thus obtained active constituents have significantly better anti-inflammatory and analgesic effect, are safer and more stable than the conventional active constituents obtained from honeysuckle flower or honeysuckle leaves, and also include sweroside which is an effective active ingredient of anti-inflammatory and analgesic drug.

Active constituents and sweroside are extracted from honeysuckle stem and purified by the following method.

A honeysuckle stem sample is reflux-extracted with about 7 to 10 volumes of distilled water for 2 to 3 hours, and then filtered. The residue is collected and reflux-extracted with about 5 to 7 volumes of distilled water for 2 to 3 hours. Thus obtained liquid is filtered and combined with the above filtrate, concentrated under reduced pressure, and filtered again, so that its volume becomes about 1 to 3 times (v/w) with reference to the herb weight. In extracting with distilled water, if distilled water is used too little, stirring becomes difficult and the extraction efficiency decreases because the solubility of the extract becomes poor. In contrast, if distilled water is used excessively, it requires more time and cost. Then, equivalent water-saturated low grade alcohol is added and stirring is carried out for about 10 to 20 minutes at 30 to 50 rpm. After the layers are separated, the water-saturated low grade alcohol layer is filtered and concentrated under reduced pressure to obtain primary active constituents. Here, the water-saturated low grade alcohol to be used is prepared by adding distilled water to low grade alcohol, such as propyl alcohol and butyl alcohol, and stirring followed by sedimentation. The process of layer separation is carried out for 2 to 3 times. In obtaining the low grade alcohol solvent fraction, if low grade alcohol is used too little, the purification efficiency decreases, thus the extraction yield and the effective ingredient content decrease. In contrast, if low grade alcohol is used too much, it results in increase in cost. Accordingly, it is recommended to use 1 to 3 volumes (v/w) of low grade alcohol with reference to the herb weight.

A column chromatography is carried out for the primary active constituents using polyamide resin, polyvinylpyrrolidone resin, and the like in order to remove unwanted materials and detect effective ingredient. The filler is used in 1 to 10 volumes (w/w) of the water-saturated low grade alcohol layer. Two three volumes of 50% (v/v) methanol and methanol to the filler volume are eluted, and then the distilled water solvent is eluted by step-gradient method. The secondary active constituents obtained by eluting the active constituents with distilled water had much less aromatic organic acids, tannins and flavonoids, and showed better medicinal effect, significantly reduced toxicity, increased solubility and improved blood stability. A column chromatography is carried out again for the secondary active constituents using ODS (octadecylsilane) resin. Starting from a 10% (v/v) methanol, 2 to 3 volumes of solvent to the resin volume is eluted by the step-gradient method while increasing the methanol content by 10% (v/v). The polyamide resin or polyvinylpyrrolidone resin is used in 20 to 50 volumes for the weight of the purified primary active constituents. The active constituents obtained by eluting 20 to 30% (v/v) methanol showed the best anti-inflammatory and analgesic effect. Analysis of the active constituents revealed that iridoid substances, such as sweroside and loganin are major active ingredients. The sweroside content was 15.1 to 72.1 wt %, and the loganin content was 13.9 to 41.4 wt %.

The active constituents obtained by eluting 20 to 30% (v/v) methanol has the highest sweroside content. Another column chromatography was carried out for these active constituents to separate sweroside represented by the following Chemical Formula 1;

(1)

For thus obtained active constituents and sweroside, an arachidonic acid induced ear edema test and a croton oil induced ear edema test were carried out to determine the anti-inflammatory effect. And, an acetic acid induced writhing test was carried out to measure the analgesic effect. As a result, they were found to have much superior inflammatory and analgesic activities than the conventional active constituents obtained from honeysuckle flower or honeysuckle leaves.

The sweroside obtained by the present invention can be prepared into treatment drugs by the methods known in the pharmaceutical circle. And, it can be administered orally or parenterally alone or along with a pharmaceutically acceptable carrier, a forming agent, a diluent, etc. Particularly, it can be prepared in the form of powder, granule, tablet, capsule, syrup, skin ointment or injection drug.

The human dosage of the active constituents or sweroside of the present invention can be selected considering the absorptivity of the active ingredient in the body, inactivation rate and excretion rate, age, sex and physical status of the subject, severity of the disease to be treated, and so forth. Preferably, the active constituents or sweroside are administered from 1 to 200 mg a day for an adult. The drug may be administered according to specialized method, if required by the experts' opinion. The drug may be administered several times a day, preferably 1 to 3 times a day, at regular intervals. The drug composition may be administered orally or non-orally. When the drug is to be administered parenterally, it can be administered through veins, muscles, rectum or skin.

Because the active constituents of honeysuckle stem have superior anti-inflammatory and analgesic effect and desirable solubility, acute toxicity and blood stability, they are well suited for the injection drug.

Hereinafter, the present invention is described in more detail through the following examples. However, the following Examples are only for the understanding of the present invention, and they shall not be construed as limiting the scope of the present invention.

EXAMPLES

Example 1

Medicinal Effects of Each Part of Honeysuckle

Samples of the whole body of honeysuckle (honeysuckle with stem and leaves), honeysuckle leaves and honeysuckle stem were taken at Yeongcheon, Gyeongsangbuk-do, Korea in July 1999. The samples were dried in the shade and reflux-extracted with 7 volumes of distilled water for 2.5 hours, and then filtered. The residue was then collected and reflux-extracted with 7 volumes of distilled water for 2.5 hours. Thus obtained liquid was filtered and combined with the above filtrate, concentrated under reduced pressure, and filtered again, so that its volume became about 2 times (v/w) with reference to the herb weight. Then, equal volume of water-saturated n-butyl alcohol was added and the mixture was stirred for 15 minutes at about 30 rpm. After the layers were separated, the alcohol layer was filtered and concentrated under reduced pressure to obtain primary active constituents. Then, a column chromatography was carried out for obtaining the purified fraction using polyamide resin (CAS NO. 63428-83-1). The resin amount was 5 volumes of the sample. Two volumes of 50% (v/v) methanol and methanol were eluted, and then the distilled water solvent was eluted by step-gradient method to obtain secondary active constituents. A croton oil induced ear edema test was carried out by administering the secondary active constituents of whole body of honeysuckle, honeysuckle stem and honeysuckle leaves into the tail veins of 6-week-old ICR mice (body weight: 20 to 30 g, n=6, SLC, Japan), which had been fasted for 4 hours. 15 minutes later, inflammation was induced with 2.5% croton oil. 4 hours later, thicknesses of left and right ears of the mice were measured using a dial thickness gauge. The rate of inflammation was calculated by the following Equation 1 and the result is shown in Table 1.

Rate of inflammation (%)=[Thickness of inflamed (right) ear−Thickness of normal (left) ear]/ [Thickness of normal ear]×100   Equation 1

TABLE 1

| Classification | Concentration (mg/kg) | Rate of Inhibition (%) |
| --- | --- | --- |
| Whole body of honeysuckle | 1 | 27.6 |
| | 3 | 29.7 |
| | 10 | 34.8 |
| | 25 | 33.6 |
| | 50 | 32.2 |
| | 100 | 30.4 |
| Honeysuckle stem | 3 | 30.2 |
| | 30 | 39.0 |
| Honeysuckle leaves | 3 | 19.6 |
| | 30 | 21.9 |

As shown in Table 1, the active constituents of honeysuckle stem showed best anti-inflammatory and analgesic activity.

Example 2

Comparison of Medicinal Effect of Active Constituents Obtained from Honeysuckle Stem A croton oil induced ear edema test was carried out as in Example 1.

Further, an arachidonic acid induced ear edema test was carried out by administering drugs (marobiven, primary constituents of honeysuckle stem, and secondary active constituents of honeysuckle stem) into the tail veins of 6-week-old ICR mice (body weight: 20 to 30 g, n=6, SLC, Japan), which had been fasted for 4 hours. Fifteen minutes later, inflammation was induced with 0.05% arachidonic acid. About 1 hour later, thicknesses of left and right ears of the mice were measured, and the rate of inhibition was calculated by Equation 1 and the result is shown in Table 2.

TABLE 2

| | | Rate of Inhibition (%) | |
| --- | --- | --- | --- |
| Classification | Dose (mg/kg) | CO* | AA** |
| Control group (marobiven) | 50 | 21.0 | NT |
| | 100 | 25.8 | NT |
| | 200 | 30.1 | NT |
| Primary active constituents | 50 | 35.6 | NT |
| | 100 | 36.2 | NT |
| | 200 | 38.0 | NT |
| Secondary active constituents | 0.1 | 19.8 | 11.7 |
| | 0.3 | 35.2 | 16.5 |
| | 3 | 38.0 | 26.3 |
| | 10 | 36.6 | 32.4 |
| | 30 | 37.1 | 48.7 |

*Croton oil induced ear edema test result
**Test result of arachidonic acid induced ear edema
NT: Not-tested As shown in Table 2, the secondary active constituents obtained from honeysuckle stem included no compounds like aromatic organic acids, tannins and flavonoids, and had a greater content of active ingredient than the primary active constituents.

Example 3

Comparison of Medicinal Effects of Active Constituents Obtained from Honeysuckle Stem The procedure of Example 1 was carried out by replacing polyamide resin with polyvinylpyrrolidone resin (CAS NO. 25249-54-1).

TABLE 3

| Classification | Dose (mg/kg) | Rate of Inhibition (%) CO* | AA** |
|---|---|---|---|
| Control group (marobiven) | 50 | 20.2 | NT |
|  | 100 | 24.1 | NT |
|  | 200 | 31.2 | NT |
| Primary active constituents | 50 | 33.2 | NT |
|  | 100 | 35.1 | NT |
|  | 200 | 37.5 | NT |
| Secondary active constituents | 0.1 | 20.1 | 10.3 |
|  | 0.3 | 34.1 | 16.7 |
|  | 3 | 39.7 | 24.9 |
|  | 10 | 35.6 | 33.3 |
|  | 30 | 36.4 | 49.6 |

*Croton oil induced ear edema test result
**Test result of arachidonic acid induced ear edema
NT: Not-tested

Example 4

Preparation of Final Active Constituents and Medicinal Effect Test

The secondary active constituents of honeysuckle stem prepared in Example 1 were concentrated under reduced pressure to obtain a powder. Another column chromatography was carried out for the powder using ODS resin (YMC*GEL ODS-A 12 nm, S-150 m or ODS-AM 12 nm, S-50 m or ODS-AQ 12 nm, S-50 m). Three volumes of resin was used and 20% (v/v) methanol was eluted to obtain the final active constituents.

A croton oil induced ear edema test was carried out as in Example 1.

Further, an acetic acid induced writhing test was carried out by administering drugs (marobiven and the final active constituents of honeysuckle stem) into the tail veins of ICR mice (body weight: 20 to 30 g, n=8, SLC, Japan), which had been fasted for a day. Twenty minutes later, 0.7% acetic acid was injected intraperioneally. Fifteen minutes later, numbers of writhing for 10 minutes were counted to calculate the rate of inhibiting inflammation. The result is shown in Table 4.

TABLE 4

| Classification | Dose (mg/kg) | Rate of Inhibition (%) CO* | AA** |
|---|---|---|---|
| Control group (marobiven) | 1 | 6.6 | 37.9 |
|  | 10 | 24.0 | 48.8 |
|  | 100 | 29.8 | 56.5 |
| Final active constituents | 0.1 | 29.6 | 62.1 |
|  | 1 | 34.8 | 68.4 |
|  | 10 | 45.8 | 76.9 |

*Croton oil induced ear edema test result
**Test result of acetic acid induced writhing
NT: Not-tested

Example 5

Contents of Active Ingredients and Medicinal Effect Test

From high performance liquid chromatography (HPLC) for the final active constituents prepared in Examples 1 and 4, the contents of active ingredient were identified: sweroside=15.1 to 72.1 wt % and loganin=13.9 to 41.4 wt %. The sweroside and loganin contents of each sample are given in Table 5. The medicinal effect of the final active constituents depending on habitat and gathering time are given in Table 6.

TABLE 5

Contents of sweroside and loganin depending on habitat and time of collection

| Month | Yeongcheon, Gyeongsangbuk-do (A) | | Andong, Gyeongsangbuk-do (B) | | Taishan, China | | Xinxiang, China | |
|---|---|---|---|---|---|---|---|---|
| January | Lo: | 34.6 | Lo: | 38.3 | Lo: | 38.2 | Lo: | 31.4 |
|  | Sw: | 57.7 | Sw: | 55.4 | Sw: | 48.6 | Sw: | 59.2 |
|  | Total: | 92.3 | Total: | 93.7 | Total: | 86.8 | Total: | 90.6 |
| February | Lo: | 30.2 | Lo: | 32.3 | Lo: | 33.3 | Lo: | 28.6 |
|  | Sw: | 64.1 | Sw: | 62.1 | Sw: | 54.2 | Sw: | 63.3 |
|  | Total: | 94.3 | Total: | 94.4 | Total: | 87.5 | Total: | 91.9 |
| March | Lo: | 22.7 | Lo: | 26.1 | Lo: | 25.8 | Lo: | 20.5 |
|  | Sw: | 70.2 | Sw: | 67.6 | Sw: | 60.3 | Sw: | 72.1 |
|  | Total: | 92.9 | Total: | 93.7 | Total: | 86.1 | Total: | 92.6 |
| April | Lo: | 13.9 | Lo: | 15.9 | Lo: | 19.1 | Lo: | 14.2 |
|  | Sw: | 63.1 | Sw: | 60.1 | Sw: | 65.3 | Sw: | 69.7 |
|  | Total: | 77.0 | Total: | 76.0 | Total: | 84.4 | Total: | 83.9 |
| May | Lo: | 17.1 | Lo: | 14.2 | Lo: | 18.7 | Lo: | 14.9 |
|  | Sw: | 52.3 | Sw: | 55.7 | Sw: | 66.2 | Sw: | 55.2 |
|  | Total: | 69.4 | Total: | 69.9 | Total: | 84.9 | Total: | 70.1 |

TABLE 5-continued

Contents of sweroside and loganin depending on habitat and time of collection

| Month | Yeongcheon, Gyeongsangbuk-do (A) | | Andong, Gyeongsangbuk-do (B) | | Taishan, China | | Xinxiang, China | |
|---|---|---|---|---|---|---|---|---|
| June | Lo: | 19.4 | Lo: | 16.2 | Lo: | 23.5 | Lo: | 17.4 |
|  | Sw: | 33.4 | Sw: | 38.2 | Sw: | 43.5 | Sw: | 42.6 |
|  | Total: | 52.8 | Total: | 54.4 | Total: | 67.0 | Total: | 60.0 |
| July | Lo: | 21.7 | Lo: | 25.3 | Lo: | 28.9 | Lo: | 22.4 |
|  | Sw: | 15.1 | Sw: | 17.5 | Sw: | 29.8 | Sw: | 35.2 |
|  | Total: | 36.8 | Total: | 42.8 | Total: | 58.7 | Total: | 57.6 |
| August | Lo: | 23.5 | Lo: | 27.0 | Lo: | 30.1 | Lo: | 32.1 |
|  | Sw: | 29.4 | Sw: | 32.7 | Sw: | 35.9 | Sw: | 36.4 |
|  | Total: | 52.9 | Total: | 59.7 | Total: | 66.0 | Total: | 68.5 |
| September | Lo: | 25.3 | Lo: | 30.1 | Lo: | 33.6 | Lo: | 39.2 |
|  | Sw: | 47.6 | Sw: | 45.3 | Sw: | 42.5 | Sw: | 40.2 |
|  | Total: | 72.9 | Total: | 75.4 | Total: | 76.1 | Total: | 79.4 |
| October | Lo: | 28.7 | Lo: | 32.2 | Lo: | 33.8 | Lo: | 37..4 |
|  | Sw: | 52.2 | Sw: | 50.5 | Sw: | 48.2 | Sw: | 43.3 |
|  | Total: | 80.9 | Total: | 82.7 | Total: | 82.0 | Total: | 80.7 |
| November | Lo: | 39.6 | Lo: | 37.3 | Lo: | 38.0 | Lo: | 41.4 |
|  | Sw: | 54.3 | Sw: | 58.3 | Sw: | 54.6 | Sw: | 45.6 |
|  | Total: | 93.9 | Total: | 95.6 | Total: | 92.6 | Total: | 87.0 |
| December | Lo: | 36.2 | Lo: | 33.7 | Lo: | 35.2 | Lo: | 40.2 |
|  | Sw: | 56.8 | Sw: | 60.2 | Sw: | 58.3 | Sw: | 52.6 |
|  | Total: | 93.0 | Total: | 93.9 | Total: | 93.5 | Total: | 92.8 |

Lo: Loganin,
Sw: Sweroside

TABLE 6

| Classification | Contents (mg/kg) | Rate of Inhibition (%) | |
|---|---|---|---|
|  |  | CO* | AA** |
| Control group (marobiven) | 10 | 25.6 | 46.9 |
|  | 100 | 28.8 | 56.8 |
| Yeongcheon, July Lo: 21.7, Sw: 15.1 Total: 36.8 | 1 | 37.2 | 70.2 |
|  | 10 | 46.3 | 75.1 |
| Andong, July Lo: 25.3, Sw: 17.5 Total: 42.8 | 1 | 40.3 | 72.2 |
|  | 10 | 51.2 | 84.3 |
| Xinxiang, July Lo: 22.4, Sw: 35.2 Total: 57.6 | 1 | 49.8 | 78.8 |
|  | 10 | 52.6 | 85.6 |
| Taishan, September Lo: 33.6, Sw: 42.5 Total: 76.1 | 1 | 52.1 | 82.9 |
|  | 10 | 52.4 | 85.5 |
| Andong, November Lo: 37.3, Sw: 58.3 Total: 95.6 | 1 | 53.4 | 84.6 |
|  | 10 | 53.2 | 87.7 |

*Croton oil induced ear edema test result
**Test result of acetic acid induced writhing Example 6

Hemolysis Test for Final Active Constituents

Twenty mL of blood was collected from a rabbit's heart using a syringe treated with heparin. The blood was centrifuged for about 10 minutes. The supernatant was discarded and the residue was diluted with 10 volumes of physiological salt solution for injection. After mixing by gentle shaking, 0.5 mL of the diluted blood and 0.5 mL of each drug of Example 1 (final active constituents of honeysuckle stem and primary active constituents of honeysuckle stem, honeysuckle leaves and whole body of honeysuckle) and the final active constituents of Example 4 were put in a test tube (Physiological salt solution and distilled water (100% hemolysis) control groups were also prepared). The test tube was incubated in a bath kept at 37° C. for 15 minutes, and then placed at room temperature for 45 minutes. Lastly, after centrifuge at 2500 rpm for 2 minutes, the upper layer was analyzed at 540 nm.

TABLE 7

| Classification | Hemolysis (%) | Standard deviation |
|---|---|---|
| Control group (physiological salt solution for injection) | 0.73 | 0.17 |
| Final active constituents, $5 \times 10^{-4}$ g/mL | 0.69 | 0.10 |
| Final active constituents, $1.5 \times 10^{-3}$ g/mL | 0.73 | 0.11 |
| Final active constituents, $5 \times 10^{-3}$ g/mL | 0.74 | 0.88 |
| Honeysuckle stem, $5 \times 10^{-3}$ g/mL | 15.2 | 0.20 |
| Honeysuckle leaves, $5 \times 10^{-3}$ g/mL | 35.1 | 0.15 |
| Whole body of honeysuckle, $5 \times 10^{-3}$ g/mL | 23.0 | 0.45 |

Example 7

Preparation of Sweroside

A column chromatography was carried out for the final active constituents prepared in Example 4 using octadecylsilane resin to separate sweroside represented by the following Chemical Formula 1;

(1)

Example 8

Determination of Anti-inflammatory Effect of Sweroside

A croton oil induced ear edema test was carried out by administering sweroside into the tail veins of 6-week-old ICR mice (body weight: 20 to 30 g, n=6, SLC, Japan), which had been fasted for 4 hours. Fifteen minutes later, inflammation was induced with 2.5% croton oil. Four hours later, thicknesses of left and right ears of the mice were measured using a dial thickness gauge. The rate of inflammation was calculated by Equation 1 and the result is shown in Table 8. The medicinal effect for oral administration is given in Table 9.

TABLE 8

| Classification | Dose (mg/kg) | Rate of Inhibition (%) |
|---|---|---|
| Sweroside | 0.1 | 49.8 |
| | 1 | 56.2 |
| | 10 | 65.7 |

TABLE 9

| Classification | Dose (mg/kg) | Rate of Inhibition (%) |
|---|---|---|
| Sweroside | 1 | 31.9 |
| | 10 | 43.1 |
| | 100 | 57.8 |

Further, an arachidonic acid induced ear edema test was carried out by administering sweroside into the tail veins of 6-week-old ICR mice (body weight: 20 to 30 g, n=6, SLC, Japan), which had been fasted for 4 hours. Fifteen minutes later, inflammation was induced with 0.05% arachidonic acid. One hour later, thickness of left and right ears of the mice was measured, and the Rate of Inhibition was calculated by the Equation 1 and the result is shown in Table 10. The medicinal effect for oral administration is given in Table 9.

TABLE 10

| Classification | Dose (mg/kg) | Rate of Inhibition (%) |
|---|---|---|
| Sweroside | 0.1 | 48.3 |
| | 1 | 55.1 |
| | 10 | 69.1 |

TABLE 11

| Classification | Dose (mg/kg) | Rate of Inhibition (%) |
|---|---|---|
| Sweroside | 1 | 29.0 |
| | 10 | 34.7 |
| | 100 | 45.7 |

Example 9

Determination of Analgesic Effect of Sweroside

An acetic acid induced writhing test was carried out by administering sweroside into the tail veins of ICR mice (body weight: 20 to 30 g, n=8, SLC, Japan), which had been fasted for a day. Twenty minutes later, 0.7% acetic acid was injected intraperioneally. Fifteen minutes later, the number of writhing for 10 minutes were counted to calculate the rate of inhibiting inflammation and the result is shown in Table 12. The medicinal effect for oral administration is given in Table 13.

TABLE 12

| Classification | Dose (mg/kg) | Rate of Inhibition (%) |
|---|---|---|
| Sweroside | 0.1 | 74.6 |
| | 1 | 86.4 |
| | 10 | 89.7 |

TABLE 13

| Classification | Dose (mg/kg) | Rate of Inhibition (%) |
|---|---|---|
| Sweroside | 1 | 65.9 |
| | 10 | 79.1 |
| | 100 | 87.9 |

Example 10

Toxicity Test

The active constituents of honeysuckle stem and sweroside, in the amount of 1.0 g/kg, 1.5 g/kg and 2.0 g/kg, were administered through the tail veins of SD rats (body weight: 120 to 170 g, 5 male and female rats for each administration dose, SLC, Japan), respectively, which had been fasted for 4 hours. The rats were observed for 30 minutes at first, and then observed at 30 minutes intervals with naked eyes. Death rate, general symptoms and weight change were observed for 2 weeks after administration. An autopsy was conducted to identify presence of any abnormalities of organs.

The lethal dose of the active constituents of honeysuckle stem and sweroside was both over 5.0 g/kg for oral administration (no dead rats observed), and over 2.0 g/kg for intravenous injection (no dead rats observed). When 2.0 g/kg was intravenously injected, the rats showed increased respiration counts and decreased activity for about 10 minutes, which were restored soon. No other symptoms were observed, and there was no change in weight due to administration. The autopsy result showed no abnormalities as is the case with the control groups.

A local toxicity test at the dose of 50, 100 and 150 mg/kg, respectively, showed no difference from the group administered with physiological salt solution. No toxicity, such as tissue necrosis or inflammation, was observed.

Preparation Example 1

Preparation of Tablet

The active constituents of honeysuckle stem or sweroside was prepared into a tablet with the following composition:

| Active ingredient | 160 mg |
|---|---|
| Light anhydrous silicic acid | 20 mg |
| Corn starch | 87 mg |
| Crystalline cellulose | 72 mg |
| Sodium starch glyconate | 60 mg |
| Magnesium stearate | 6 mg |
| Total | 672 mg |

Preparation Example 2

Preparation of Syrup

The active constituents of honeysuckle stem or sweroside was prepared into syrup with the following composition:

| Active ingredient | 4,000 mg |
|---|---|
| Methyl p-oxybenzoate (5% ethanol solution) | 60 mg |
| Propyl p-oxybenzoate (5% ethanol solution) | 40 mg |
| Sodium benzoate (5% solution) | 100 mg |
| Banana powder (10% solution) | 600 mg |
| D-Sorbitol | 140,000 mg |
| Distilled water | 196 mL |

Preparation Example 3

Preparation of Injection

The active constituents of honeysuckle stem or sweroside was prepared into an injection with the following composition:

| Injection ampule: | Active ingredient | 20 mg |
|---|---|---|
| | Mannitol | 60 mg |
| Corresponding solvent sample: | Physiological salt solution for injection | 2000 mg |
| | Total | 2080 mg |

Preparation Example 4

Preparation of Injection

The active constituents of honeysuckle stem or sweroside was prepared into an injection with the following composition:

| Injection ampule: | Active ingredient | 50 mg |
|---|---|---|
| | $KH_2(PO_4)$ | 8.5 mg |
| | Physiological salt solution for injection | 3000 mg |
| | Total | 3058.5 mg |

Preparation Example 5

Preparation of Injection

The active constituents of honeysuckle stem or sweroside was prepared into an injection with the following composition:

| Injection ampule: | Active ingredient | 100 mg |
|---|---|---|
| | Mannitol | 300 mg |
| | $KH_2(PO_4)$ | 17 mg |
| | Physiological salt solution for injection | 3000 mg |
| | Total | 3417 mg |

Preparation Example 6

Preparation of Ointment Drug

The active constituents of honeysuckle stem or sweroside was prepared into an ointment drug the following composition:

| Active ingredient | 5 g |
|---|---|
| Liquid paraffin | 10 g |
| Hard lead | 9 g |
| Ethanol | 8 g |
| Sorbitan monooleate | 2 g |
| Polysorbate | 4 g |
| Propyl p-oxybenzoate | 0.05 g |
| Methyl p-oxybenzoate | 0.1 g |
| Concentrated glycerine | 10 g |
| Purified water | Adequate |

As described above, the active constituents of the present invention obtained from honeysuckle stem have significantly increased solubility and blood stability as compared to those of the conventional active constituents. Further, they are shown to have superior analgesic and anti-inflammatory effect, safety and stability. Also, sweroside of the present invention obtained from honeysuckle stem has very superior medicinal effect and shows little toxicity, thus being very suitable for an anti-inflammatory and analgesic drug.

While the present invention has been described in detail with reference to the preferred embodiments, those skilled in the art will appreciate that various modifications and substitutions can be made thereto without departing from the spirit and scope of the present invention as set forth in the appended claims.

What is claimed is:

1. A preparation method of active constituents of honeysuckle stem, which comprises:
   (a) a step of reflux-extracting honeysuckle stem with water, filtering it, carrying out layer separation by adding equivalent water-saturated low grade alcohol to said filtrate, and concentrating it under reduced pressure; and
   (b) a step of purifying the concentrated filtrate with polyamide resin or polyvinylpyrrolidone resin, and then purifying again with octadecylsilane resin to obtain secondary active constituents,
   wherein said active constituents comprises iridoid glycosides.

2. The preparation method of active constituents of honeysuckle stem according to claim 1, wherein said water-saturated low grade alcohol is saturated propyl alcohol or butyl alcohol solution.

3. The preparation method of active constituents of honeysuckle stem according to claim 1, wherein said active constituents comprise sweroside and loganin.

4. The preparation method of active constituents of honeysuckle stem according to claim 3, wherein said active constituents comprise 15.1 to 72.1 wt % of sweroside and 13.9 to 41.4 wt % of loganin.

5. An anti-inflammatory and analgesic drug which comprises said active constituents of honeysuckle stem prepared by the method according to claim 1 sweroside and loganin as effective active ingredients, wherein the drug is administered alone or with a pharmaceutically acceptable carrier.

6. The anti-inflammatory and analgesic drug according to claim 5, wherein said active constituents comprise 15.1 to 72.1 wt % of sweroside and 13.9 to 41.4 wt % of loganin.

7. The anti-inflammatory and analgesic drug according to claim 5, which is prepared in the form of tablet, powder, granule, capsule, syrup, skin ointment or injection.

* * * * *